United States Patent [19]

Verdini et al.

[11] Patent Number: 5,219,987
[45] Date of Patent: Jun. 15, 1993

[54] SEQUENTIAL POLYPEPTIDES ENDOWED WITH IMMUNOLOGICAL ACTIVITY

[75] Inventors: Antonio S. Verdini, Monterotondo; Antonello Pessi; Fabio Bonelli, both of Rome, all of Italy

[73] Assignee: Eniricerche S.p.A., Milan, Italy

[21] Appl. No.: 227,364

[22] Filed: Aug. 2, 1988

[30] Foreign Application Priority Data

Sep. 11, 1987 [IT] Italy ................. 21892 A/87

[51] Int. Cl.$^5$ ............... A61K 37/02; C07K 7/06; C07K 7/08/7/10
[52] U.S. Cl. ................. 530/324; 530/325; 530/326; 530/327; 530/328; 530/329; 424/88
[58] Field of Search ........... 530/324, 325, 326, 327, 530/328, 329; 424/88

[56] References Cited

U.S. PATENT DOCUMENTS

| | | | |
|---|---|---|---|
| 3,929,756 | 12/1975 | Leeman et al. | 530/327 |
| 4,132,746 | 6/1979 | Urry et al. | 525/432 |
| 4,409,141 | 11/1983 | Noda et al. | 435/7 |
| 4,707,357 | 11/1987 | Dame et al. | 530/324 |
| 4,843,146 | 6/1989 | Bernardi et al. | 435/7 |

OTHER PUBLICATIONS

Chou, Peter Y, et al., *Ann. Rev. Biochem.*, 47: 251–76, 1978.
Hopp, Thomas P., *J. of Immun. Methods*, 88: 1–18, 1986.
Chou & Fasman Algorithm, Intelli Genetics.

*Primary Examiner*—Howard E. Schain
*Attorney, Agent, or Firm*—Shea & Gould

[57] ABSTRACT

Synthetic polypeptides constituted by at least two consecutive repeating units of (Asn-Asn-Pro) sequence are powerful immunogens in test animals.

The formed antibodies recognize both the synthetic polypeptides and the immuno-dominant epitope of the circumsporozoitic protein of *Plasmodium falciparum*.

Said polypeptides, which can be obtained in pure form, are particularly useful for the preparation of antimalarial vaccines and of diagnostic kits for the determination of malarial affections.

3 Claims, No Drawings

SEQUENTIAL POLYPEPTIDES ENDOWED WITH IMMUNOLOGICAL ACTIVITY

The present invention relates to synthetic polypeptides endowed with immunological activity, useful in the sector of malaria.

In particular, the present invention relates to synthetic polypeptides capable of inducting in mammals a high-titre antibody response, specific not only against them, but also against the immuno-dominant epitope of the circumsporozoitic protein of Plasmodium falciparum.

The present invention also relates to the use of said polypeptides for the preparation of antimalarial vaccines and of diagnostic kits for the detection of antimalarial-parasite antibodies in clinical samples.

Malaria, caused by a protozoan of Plasmodium genus, presently represents one of most serious parasitical diseases in man.

This disease is reckoned, indeed, to strike, each year, form 100 to 200 millions of individuals, causing a mortality rate in early infancy which may reach 50% of cases.

Among the fours species of man-infecting Plasmodium, the most common are P. vivax and P. falciparum.

This latter, in particular, causes most diseases and deaths associated with malaria, and due to this reason, a vaccine against such a type of etiologic agent is particularly desired.

The infection begins in man with the inoculation, by the mosquito, of sporozoites, which rapidly settle in the hepatic cells. Here, each sporozoite originates 20,000, or more, merozoites, each of which, after leaving the hepatic cell, is capable of infecting an erythrocyte. Inside the erythrocyte, the parasite is asexually reproduced from rings to schizonts.

The mature schizont contains single merozoites capable of invading other erythrocytes.

Such a cyclo of repeated breakage of the erythrocytes by the asexual parasites causes the clinical manifestations.

Some merozoites, instead of continuing to protliferate, differentiate into gametocytes, which represent the infecting form for mosquitos.

The complex structure and the vital cycle of the malarial parasites have made it difficult, up to date, to solve the problem of an efficacious antimalarial vaccine.

In fact, the malarial parasites develop according to a multi-step cycle, and present to the host an extremely large number of antigenic components, and each form of development of the parasite contains antigens different from one another and step-specific.

In their attempts to identify plasmodial antigens, researchers have focused their interest towards those antigens which are exposed to the immunittary system, and are both present on the surface of the parasite, and on the membrane of the infected erythrocyte.

Particularly interesting was the study of the sporozoites of Plasmodium, in that the preparation of an antisoporozoite vaccine, if endowed with complete efficacy, is capable of preventing the development of the Plasmodium in the host organism, and hence of inducing a sterile immunity.

Attempts of antisporozoitic vaccination on animals and man were carried out by using sporozoites of P. falciparum and P. vivax irradiated with X-rays, with a protective, non-strain-specific immunity against the disease being obtained.

However, a so-formulated vaccine appears not very suitable for a large-scale application, owing to both the limited availability of the sporozoites, and their instability.

The use of monoclonal antibodies made it possible the major surface protein of sporozoites of P. berghei (N. Yoshida, R. S. Nussenweig et al. (1980), Science 209, 71) and of other protozoans infective for animals and for man, including P. falciparum (F. Santoro et al. (1983), J. Biol. Chem. 258, 3341), to be identified.

This protein, denominated as "circumsporozoitic protein", or CS, completely covers the surface of the sporozoite, and induces a specific antibody response which supplies a protection against malarial infections.

Recently, in patent application EP 166,410, the cloning and sequencing of the gene coding for the CS protein of P. Falciparum was disclosed, and the fact was stressed that the immuno-dominant epitope present inside it is constituted by the Asn-Ala-Asn-Pro (NANP) tetrapeptide repeated 37 times and by 4 Asn-Val-Asp-Pro (NVDP) quartets.

It was furthermore reported that peptides containing such repeated sequences, obtained via recombinant DNA, were capable of inducing the formation in vivo of anti-$(NANP)_n$ antibodies, which in vitro inhibited the penetration of the hepatocytes by the sporozoites, and were recognized by mono- and poly-clonal antisporozoite antibodies.

Therefore, said peptides appeared to be particularly useful immunogens for the preparation of an antisoporozoite vaccine.

However, the use of proteins obtained by cultivating host organisms transformed by means of the recombinant-DNA techniques, suffers from drawbacks which derive both from the difficulty of purification of the obtained product, and from the presence, inside it, of aminoacid sequences foreign to native CS protein.

Therefore, other processes were proposed in the prior art for the preparation of immunologically active peptides containing said repeated sequences.

Co-pending U.S. patent application No. 850.135 discloses and claims sequential peptides, which are constituted by the (NANP) tetrapeptide repeated n times, preferably 40 times, and are obtained by means of a polycondensation process.

Said peptides are recognized by antisoporozoite antibodies present in the serum of individuals exposed to malarial infections, and are capable of inducing the formation of anti-$(NANP)_n$ antibodies in animals, even when they are not conjugated with a proteinic support.

However, vaccines containing said peptides are not at all satisfactory, in particular on considering the fact that the immunitary response to said synthetic immunogens results, in mice, subject to genetic restrictions.

In fact, it was observed that only those mice, in whose genetic complement the I-$A^b$ gene is present, recognize the T epitope contained in the repeated sequence of CS protein, and are therefore capable of producing an anti-$(NANP)_n$ antibody response.

It is known, in fact, that, in order that an antibody response may be generated against any polypeptidic immunogens, a cellular cooperation must exist between the lymphocytes of T-helper type, and the antibody-producer B lymphocytes, each one activated by the recognition of its epitopes.

These results obtained in mice induced the researchers to regard such synthetic vaccines as not very suitable for supplying man with a general protection, in that, even if the immunitary response in man was under genetic control, the possible production of protective antibodies, under condition of cellular "boosting" caused by the bite of infect mosquitos would only occur in "responder" individuals.

The search for efficacious antimalarial synthetic vaccines is therefore oriented towards the synthesis of more complex peptides, in the molecule of which besides the $(NANP)_n$ sequence, considered the main B site of CS protein, also peptidic sequences of the CS protein are present, which are capable of being recognized by the T cells, and, therefore, of inducing a high secondary antibody response as a consequence of the inoculation of the sporozoite, and hence of the native protein, by the mosquito.

Such complex polypeptides, containing a combination of epitopes specific for the B cells and the T cells, are considered as critically important also for a protection not only depending on the specific anti-$(NANP)_n$ antibodies, but also on aspecitific factors produced by the T cells, such as interleukins and the like, and on the activation of cytotoxic T cells, which can play an important role in the immunity against the sporozoite.

Recently, M. F. Good et al. (Science, 236, 1059 (1987)) have prepared a synthetic immunogen constituted by the PSDKHEIQYLKKIKNSIS sequence, bonded, by means of a covalent bond, to the NP(NANP)₅NA sequence.

Such an immunogen is capable of causing anti-$(NANP)_n$ antibodies to be formed in two strains of mice non-responders to pure $(NANP)_n$.

There result indicate hence that in the sequence of the CS protein some main epitopes are present, beyond $(NANP)_n$, which are capable of both stimulating the T cells, as well as helping the B cells to produce anti-$(NANP)_n$ antibodies, and of causing the T cells proliferation, which is important for the antibody-independent cellular immunity.

The present Applicant has found now that sequential polypeptides containing the aminoacid residues of the dominant epitope of CS protein, $(NANP)_n$, less those of alanin (Ala), are potential immunogens.

Therefore, a purpose of the present invention are polypeptides endowed with immunological activity, capable of inducing in mammals a high-titre antibody response, useful in the sector of malaria.

Another purpose of the present invention is a process for preparing said synthetic polypeptides.

Still another purpose of the present invention is the use of said sequential polypeptides for the preparation of an anti-malarial vaccine.

A further purpose of the present invention is the use of said sequential polypeptides for preparing diagnostic kits for the determination of antisporozoite antibodies in clinical human samples.

Still further purposes of the present invention will be clear from the reading of the text and of the following examples.

In particular, the polypeptides according to the present invention are constituted by at least two consecutive repeating units of H—Asn—Asn—Pro—OH sequence, wherein:

Asn is L-asparagine, and
Pro is L-proline,
and can be defined by means of the formula:

$$H-(Asn-Asn-Pro)_n-OH \qquad (I)$$

According to the present invention, said polypeptides can be prepared by means of a process which comprises:
a) the synthesis of a tripeptide protected at the end amino-group of Asn, having the following formula:

$$X-Asn-Asn-Pro-OH \qquad (II)$$

wherein X is an acid-labile protecting group;
b) the activation of the tripeptide (II) by means of the reaction with halogenated derivatives of phenol, in order to form the active ester of said tripeptide at the end carboxy group of Pro, having the following formula:

$$X-Asn-Asn-Pro-OY \qquad (III)$$

wherein:
X has the above-stated meaning; and
Y is the radical of the halogenated derivative of phenol;
c) the removal of the protecting group from said tripeptide (III) by acidic cleavage, in order to obtain the tripeptide:

$$HCl.H-Asn-Asn-Pro-OY \qquad (IV)$$

d) the polycondensation of said tripeptide (IV) in the presence of a base of organic nature, and finally
e) the separation by chromatography of the fractions which contain the polypeptide consisting of at least two consecutive repeated units of Asn—Asn—Pro sequence.

The (a) Step

In the (a) step of the process according to the present invention, the tripeptide (II) is prepared by condensation in homogeneous phase according to one of the general techniques known in the art.

In practice, the preparation is carried out by dissolving in an inert (non-reactive) organic solvent the aminoacids, suitably protected at their reactive functions, in the presence of condensation agents.

Organic solvents suitable for the intended purpose are selected from chlorinated aliphatic hydrocarbons, aliphatic aldehydes, alkyl esters.

Specific examples of such solvents are N,N-dimethylformamide, chloroform, ethyl acetate, tetrahydrofuran.

Protecting groups for the aminic functions are generally selected from those which can be removed by means of an acidic hydrolysis (acid-labile groups).

Among these, particularly preferred is tert.-butyloxycarbonyl (Boc), which can be removed under mild hydrolysis conditions.

The temperatures at which the condensation reaction is carried out are generally comprised within the range of from $-10°$ C. to $40°$ C., and the corresponding times are those times which are required in order to complete, or substantially complete, the reaction.

The (b) Step

In the (b) step of the process according to the present invention, the tripeptide (II) protected at the end amino-group is activated by means of the reaction with a derivative of phenol, in order to form the active ester of said tripeptide at the end carboxy group of Pro:

X—Asn—Asn—Pro—OY     (III)

wherein

X has the above indicated meaning, and

Y is the radical of the halogenated derivative of phenol.

Halogenated derivatives of phenol which can be used in the process according to the present invention are the fluorinated or chlorinated derivatives of phenol.

Particularly useful for the intended purpose are pentachloro-phenol, trichloro-phenol and pentafluoro-phenol.

The reaction of activation at the carboxy group of Pro is carried out by bringing the tripeptide (II) into contact with the halogenated derivative of phenol, in a mutual molar ratio equal to, or approximately equal to, 1, in a liquid medium in an organic solvent and at a temperature comprised within the range of from $-10°$ C. to $40°$ C. The reaction is preferably carried out at room temperature ($20°-25°$ C.), or at temperatures close to room temperature.

Examples of organic solvents suitable for the intended purpose are selected from the aprotic solvents, such as ethyl acetate, or aliphatic hydrocarbons, or DMF.

The so-obtained solution is cooled to a temperature of approximately $0°$ C., and to it a condensation agent is subsequently added, with the molar ratio between the condensing agent, and either of the starting ractants, being equal to, or approximately equal to, 1.

The preferred condensation agent is dicyclohexylcarbo-diimide (DCCI).

The so-obtained solution is then maintained at a temperature comprised within the range of from $-10°$ C. to $40°$ C. for a time comprised within the range of from 4 hours to 15 minutes.

At the end of the reaction, the dicyclohexyl-urea (DCU) formed during the same reaction is separated from the reaction mixture, and the solvent is evaporated off.

The obtained residue is then purified by crystallization with isopropyl alcohol and ethyl acetate.

A product is thus obtained with a yield of approximately 94%, which at $H^1$—N.M.R. and mass spectroscopy shows the expected structure.

The (c) Step

In the (c) step of the process according to the present invention, the protecting group is removed from the terminal aminic group of tripeptide (III) to means of an acidic hydrolysis.

The reaction is carried out by using trifluoroacetic acid or a solution of hydrochloric acid in ethyl acetate, and at room temperature ($20°-25°$ C.), for a reaction time of approximately 1 hour.

Through the solution, nitrogen is then bubbled for a time comprised within the range of from 30 minutes to 60 minutes, and from the reaction mixture, the precipitated product is then separated, repeatedly washed and concentrated to dryness under vacuum.

The product di formula (IV) is thus obtained, with a yield of approximately 91%; at T.L.C. analysis, it shows to be homogeneous.

The (d) Step

In this step, the activated and deprotected tripeptide (IV) is dissolved in the liquid phase in an organic solvent, and is polycondensed in the presence of a base of organic nature.

Suitable organic bases for the intended purpose are the tertiary alkyl-amines, wherein the alkyl group is formed by a number of carbon atoms comprised within the range of from 1 to 4.

Particularly preferred is triethyl-amine.

The polycondensation reaction is carried out in an organic solvent selected from dimethyl-sulphoxide, dimethyl-formamide or hexamethyl-phosphoramide, at temperatures comprised within the range of from $-10°$ C. to $40°$ C. for a time of from 4 days to 24 hours.

In practice, the reaction is carried out at room temperature, or at a temperature close to room temperature, and, in this case, the required times for completing or substantially completing the reaction are of the order of 96 hours.

When the polycondensation reaction is ended, the solution is dropwise added to absolute ethyl alcohol kept with mild stirring, and the so-obtained white precipitate is filtered off, washed and dried under vacuum.

The dried product is then dissolved in a water/dioxane solution and is freeze-dried.

The lyophil, constituted by a mixture of polypeptides having different molecular weights, can be used as such for the preparation of antimalarial vaccines, and of diagnostic kits, or it can be fractionated according to general techniques known in the art, so as to obtain polypeptides with a narrower distribution of molecular weight (M.W.) (the (e) step).

The (e) Step

In particular, according to the present invention the fraction of the lyophil is carried out by chromatography on a column of Sephadex ® G-50, at a temperature of $20°-25°$ C., eluting with 0.1 M acetic acid, with a flow rate of 36 ml/hour.

By operating in such a way, collected and separated are fractions which correspond to a molecular weight of 1,600—corresponding to polypeptides constituted by 4 tripeptides—, and fractions with a molecular weight of approximately 4,000—corresponding to polypeptides constituted by $11\pm2$ consecutive tripeptides.

All these peptides are particularly useful for the purposes of the present invention.

Particularly suitable are the $(NNP)_{11}$ polypeptides, which in laboratory animals show to be extremely powerful immunogens.

The antibodies, produced at a high titre, recognize, besides the synthetic antigen $(NNP)_{11}$, also the $(NANP)_{40}$ antigen.

These results show that the $(NNP)_n$ sequence contains an epitope capable of very efficaciously stimulating the B cells in the production of anti-$(NANP)_{40}$ antibodies and, consequently, capable of stimulating the T-helper cells too.

Such a property makes the sequential polypeptides of the present invention particularly suitable for the development of synthetic antisporozoite vaccines.

The sequential polypeptides according to the present invention can be used as such, or they can be incorporated in a more complex vaccine constituted by different epitopes.

The following experimental examples are illustrative and non-limitative of the invention.

EXAMPLE 1

Synthesis of Peptide:
t.-Butyl-oxy-carbonyl-L-Asparagin-yl-L-Asparaginyl-L-Proline (Boc-Asn-Asn-Pro-OH)

a) Synthesis of t.-butyl-oxycarbonyl-L-asparaginyl-L-proline benzyl-ester (Boc-Asn-Pro-OBzl)

24.06 g (100 mmol) of HCl.ProOBzL, 25.5 g (110 mmol) of Boc-Asn-OH, 16.2 g (120 mmol) of 1-hydroxybenzotriazole (HOBt) and 12,12 ml (110 mmol) of N-methyl-morpholine (NMM) are dissolved in 350 ml of N,N-dimethyl-formamide (DMF).

The solution is cooled to 0° C. and to it, 22.7 g (110 mmol) of dicyclohexyl-carbodiimide (DCCI) dissolved in 60 ml of DMF is added.

The solution is then heated up to a temperature of 20° C. and the reaction is let proceed for 16 hours at this temperature, with stirring.

At the end of said time period, the reaction mixture is filtered in order to remove the precipitated dicyclohexyl-urea (DCU) and the solvent is evaporated to dryness.

The so-obtained residue is collected in 30 ml of ethyl acetate (EtOAc), and is extracted, in succession, twice with 5 ml of an aqueous solution of $NaHCO_3$ (at 5% w/v), twice with 5 ml of an aqueous solution of citric acid (5%, w/v) and with water, until for the water phase a neutral pH is obtained.

The organic phase is then separated, is thoroughly dried with approximately 10 g of anhydrous $MgSO_4$, and is concentrated under vacuum.

By operating as above reported, a gel-like residue is obtained, which is subsequently washed with EtOAc, and is triturated with 20 ml of ethyl ether ($Et_2O$), until a white solid is obtained, which is dried under vacuum.

30.6 g (73 mmol) (73%) of the desired product with a melting point of 106°–108° C. is obtained.

The analytical data (T.L.C., H.P.L.C and $H^1$-N.M.R.) confirm the identity and the purity of the product.

b) Synthesis of asparaginyl-L-proline-benzyl-ester hydrochloride (HCl.H-Asn-Pro-OBzl)

20.32 g (48.4 mmol) of Boc-Asn-Pro-OBzl obtained as reported in previous (a) step is reacted with 200 ml of EtOAc saturated with HCl, at 20° C. for 1 hour. At the end of said time, through the solution, kept stirred and maintained at room temperature (20°–25° C.), anhydrous nitrogen is bubbled for approximately 3 hours.

A white precipitate is thus obtained, which is filtered off from the reaction mixture, is repeatedly washed with $Et_2O$ and is finally dried under vacuum for 20 hours.

Yield: 16.4 g (45.9 mmol), 95% $[\alpha]_D^{20} = -50.2°$ (c=1, DMF).

c) Synthesis of t.-butyloxycarbonyl-L-asparaginyl-L-asparaginyl-L-proline-benzyl-ester (Boc-Asn-Asn-Pro-Obzl)

16.4 g (45.9 mmol) of the compound: HCl.Asn-Pro-OBzl obtained in previous (b) step is dissolved in 250 ml of DMF together with 11.75 g (50.6 mmol) of Boc-Asn-OH, 7.47 g (55.2 mmol) of HOBt and 5.57 ml (50.6 mmol) of NMM.

To the solution, cooled down to 0° C., 50 ml of DMF containing 10.44 g (50.6 mmol) of DCCI is then added. The solution is maintained for 16 hours at 20° C. with stirring.

The DCU formed is then separated from the reaction mixture, the solvent is evaporated under vacuum, the residue is suspended with 30 ml of EtOAc and the so-obtained finely subdivided suspension is filtered off from the solvent.

The resulting solid, characterized by $H^1$-N.M.R., is in accordance with the proposed structure, and, furthermore, at T.L.C. it results homogeneous (butanol/water/acetic acid, 4:1:1); $R_f = 0.27$.

The so-obtained product has a melting point of 175°–177° C. and an $[\alpha]_D^{20} = -48.8°$ (c=1, DMF).

d) Synthesis of t.-butyloxycarbonyl-L-asparaginyl-L-asparaginyl-L-proline (Boc-Asn-Asn-Pro-OH)

To a reaction vessel having 200 ml of capacity, and fitted with stirring means, 100 ml of DMF, 5.0 g (9.35 mmol) of Boc-Asn-Asn-Pro-OBzl and 2 g of Pd catalyst (10% of Pd on coal) are charged.

The mass inside the flask is stirred, and a suspension is obtained.

Through said suspension, kept stirred at 25° C., hydrogen gas is then bubbled for 7 hours.

When the reaction is ended, the catalyst is filtered off, and the solvent is evaporated to dryness.

4.07 g (9.16 mmol) (98%) of an oily, colourless and T.L.C.-homogeneous product is obtained.

EXAMPLE 2

Synthesis of the Sequential Polypeptide:
Poly-(L-asparaginyl-L-Asparaginyl-L-Proline)

a) Synthesis of t.-butyl-oxy-carbonyl-L-asparaginyl-L-asparaginyl-L-proline pentachlorophenylester (Boc-Asn-Asn-Pro-OPCP)

4.07 g (9.16 mmol) of Boc-Asn-Asn-Pro-OH obtained as reported in Example 1, is dissolved in 150 ml of DMF containing 2.71 g (10.2 mmol) of pentacloro-phenol. The solution is cooled down to 0° C., to is 25 ml of DMF containing 1.92 g (9.3 mmol) of DCCI is added, and the whole mixture is maintained at this temperature for 16 hours.

From the reaction mixture, the precipitated off DCU is then separated, and the solvent is evaporated under vacuum.

The so-obtained residue is treated at approximately 70° C. with 100 ml of isopropyl alcohol and then with EtOAc, up to early crystallization.

5.96 g (8.6 mmol) (93.8%) is obtained, of a white solid having a melting point of 180°–181° C., and an $[\alpha]_D^{20} = -49.9°$ (c=1, DMF).

The product characterized by $H^1$-N.M.R. and mass-spectroscopy, has the expected structure, and it is furthermore homogeneous at T.L.C. (butanol/water/acetic acid, 4:1:1); $R_f = 0.56$.

b) Synthesis of L-asparaginyl-L-asparaginyl-L-proline pentachloro-phenyl-ester hydrochloride (HCl.H-Asn-Asn-Pro-OPCP)

5.75 g (8.3 mmol) of Boc-Asn-Asn-Pro-OPCP is dissolved in 100 ml of EtOAc saturated with HCl, and the resulting solution is reacted at room temperature for 1 hour.

After a 3-hour bubbling of nitrogen through the solution, the precipitated product is filtered off, is repeatedly washed with Et$_2$O and is finally evaporated to dryness under vacuum for 16 hours.

4.76 g (7.57 mmol) (91%) is obtained of the expected product, which decomposes within a temperature range of from 213° to 217° C. and has an $[\alpha]_D^{20} = -54.9°$ (c=1, DMF).

When analysed in by T.L.C., the product shows to be homogeneous.

C. Synthesis of poly-(L-asparaginyl-L-asparaginyl-L-proline)

(Poly-(Asn-Asn-Pro)-OH)

2.5 g (3.97 mmol) of HCl.H-Asn-Asn-Prop-OPCP obtained as reported in the (b) step is dissolved in 5 ml of dimethyl-sulphoxide (DMSO), to it 0.55 ml of triethylamine (TEA) is added, and the resulting mixture is maintained, with slight stirring, at 20° C. for 96 hours.

At the end of the reaction, the solution, which is viscous and opalescent, is added dropwise, over a time of, or approximately of, 5 minutes, to 200 ml of absolute EtOH kept mildly stirred.

A white precipitate is thus obtained, which is filtered off, is washed with EtOH, and is dried under vacuum.

The solid is then dissolved in 30 ml of water/dioxane (5:2, V/V) and is freeze-dried.

Fractions of approximately 50 mg of the so-obtained lyophil are then dissolved in 2 ml of 0.1 M acetic acid and are chromatographed on a column (85 cm × 2.6 cm) of Sephadex ® G-50 (Pharmacia), at room temperature (20°-25° C.), are eluted with 0.1 M acetic acid at a flow rate of 36 ml/hour, and with the fractions being collected at time intervals of 5 minutes.

The first fractions eluted from the column are combined with one another, and are freeze-dried, with a total amount of 100 mg of the polypeptide being obtained, which has an average molecular weight of approximately 4,000 KD, corresponding to a number of repeating (Asn-Asn-Pro) units of 11±2.

The molecular weight of said fraction is verified by chromatography on agarose column BIOGEL A5M (BIORAD) (86×0.8 cm), equilibrated with 6 M guanidinium chloride, eluting at a flow rate of 2.5 ml/hour, and using standards having a known molecular weight comprised within the range of from 70,000 to 3,000 KD.

EXAMPLE 3

The capability of (Asn-Asn-Pro)$_{11}$ ((NNP)$_{11}$) to induce an antibody response in test animals is tested by immunizing 5-week-old male rabbits with the synthetic polypeptide, whilst the specificity of the antibodies formed in determined by means of the immunoenzymatic ELISA test, with both (Asn-Asn-Pro)$_{11}$ and (Asn-Ala-Asn-Pro)$_{40}$ —which reproduces the immunodominant epitope of the CS protein of *Plasmodium falciparum*, synthesized as disclosed in U.S. patent application Ser. No. 850,135 Apr. 10, 1986—being used.

The rabbits (6) are inoculated by intramuscular way (1 inoculum) and by subcutaneous way (4 inoculi), with respectively 3 rabbits being inoculated with 1 ml of phosphate buffer saline at pH 7.8 (PBS) containing 1 mg of (NNP)$_{11}$ + 1 ml of complete Freund adjuvant (CFA) and 3 rabbits (control) being inoculated with 1 ml of PBS + 1 ml of CFA.

After 21 days of the first inoculum, the animals ar inoculated again, with the same doses and according to the same modalities as above reported.

At the 35th day of the first inoculum, into the animals is injected by intramuscular way and by subcutaneous way 1 ml of PBS containing 1 mg of (NNP)$_{11}$, to which 1 ml of incomplete Freund adjuvant is added.

The sera of the so-treated animals are drawn on days 0, 20, 34 and 48, and are analyzed by means of the ELISA test, in order to quantify the antibodies formed, and to test them for their specificity.

In practice, the synthetic antigens (NANP)($_{40}$ and (NNP)$_{11}$ are made adsorb in wells of polystyrene plates for microtitration (Nunc-immunoplate I, Nunc, Roskilde, Danemark), with 50 μl of PBS solution containing 4 μg/ml of said antigens being distributed in each well, and with the plates being maintained at room temperature for 16 hours.

The plates are then washed 3 times with PBS-Tween (0.05% of Tween at 20 v/v, pH 7.4), and the aspecific binding sites are blocked by incubation at room temperature for 1 hour with BPS-Tween-1% (w/v) of milk powder.

Scalar dilutions of rabbit serum are prepared in 100 μl of PBS-1% of milk powder and 50 μl of each dilution is inoculated to the wells of the microplates and incubated at room temperature for 1 hour.

After the incubation, the plates are washed 3 times with PBS-Tween, and are incubated with 50 μl of rabbit anti-Ig antibody diluted in PBS-Tween-milk powder, at room temperature for 1 hour.

The plates are washed again as above reported, and to each well 50 μl is then added of peroxidase-antiperoxidase complexes suscitated in rabbit, diluted in PBS-Tween-milk.

The plates are incubated at room temperature for 1 hour and are then washed 3 times with PBS-Tween.

Finally, to the plates, 30 μl of ortho-phenylenediamine in methanol + hydrogen peroxide are added to the plates and, after approximately 30 minutes, the absorbance of the solutions at 492 nm is determined on an ELISA reading instrument.

The results obtained are reported in following Table

TABLE 1

| | ANTIBODY TITRE | |
|---|---|---|
| | Anti-(NANP)$_{40}$ | Anti-(NNP)$_{11}$ |
| Before immunization | 0 | 0 |
| 20th day | 1:8,000 | 1:1,280 |
| 34th day | 1:50,000 | 1:5,120 |
| 48th day | 1:100,000 | 1:10,240 |
| Control | 0 | 0 |

From the above, the synthetic polypeptide (NNP)$_{11}$ results to be a powerful immunogen in test animals, capable of inducing a high-titre antibody response not only against itself, but also against the synthetic antigen (NANP)$_{40}$.

We claim:

1. Synthetic, sequential polypeptides endowed with immunological activity, capable of inducing in mammals a high-titre antibody response against the circumsporozoitic protein of Plasmodium, which can be defined by means of the formula:

$$H-(Asn-Asn-Pro)_n-OH \quad (I)$$

wherein:
Asn is L-asparagine, and
Pro is L-proline, and
n as has value not less than 2.

2. Synthetic, sequential polypeptides according to claim 1, wherein n is not greater than 100.

3. Synthetic, sequential polypeptides according to claims 1 and 2, wherein n is 11.

* * * * *